United States Patent
Barton

[11] Patent Number: 5,941,385
[45] Date of Patent: Aug. 24, 1999

[54] COLLAPSIBLE SHARPS CONTAINER WITH HOLDER

[76] Inventor: Cheryl L. Barton, 1233 Daniels Rd., Pavo, Ga. 31778

[21] Appl. No.: 08/966,759

[22] Filed: Nov. 10, 1997

[51] Int. Cl.⁶ .................................................. B65D 83/10
[52] U.S. Cl. .......................... 206/366; 206/370; 220/375; 220/667; 220/735
[58] Field of Search ..................... 206/366, 373, 206/365, 370, 438; 220/908, 375, 666, 667, 729, 735, 694, 697

[56] References Cited

U.S. PATENT DOCUMENTS

| | | | |
|---|---|---|---|
| 331,999 | 12/1885 | Perry | 220/375 |
| 906,644 | 12/1908 | Meade | 220/735 |
| 2,594,176 | 4/1952 | Kaiser, Jr. | 220/735 |
| 3,282,477 | 11/1966 | Henchert | 220/339 |
| 3,939,887 | 2/1976 | Scarnato | 150/5 |
| 3,939,888 | 2/1976 | Scarnato | 150/5 |
| 4,429,789 | 2/1984 | Puckett, Jr. | 206/370 |
| 4,667,821 | 5/1987 | Shillington | 206/366 |
| 4,930,631 | 6/1990 | Bruno . | |
| 4,934,556 | 6/1990 | Kleissendorf | 220/269 |
| 4,982,843 | 1/1991 | Jones . | |
| 5,103,997 | 4/1992 | Shillington et al. . | |
| 5,127,522 | 7/1992 | Ranford . | |
| 5,145,063 | 9/1992 | Lee . | |
| 5,240,108 | 8/1993 | Tonna . | |
| 5,281,391 | 1/1994 | Hanson et al. . | |
| 5,413,243 | 5/1995 | Bemis et al. . | |
| 5,419,435 | 5/1995 | Perzan et al. . | |
| 5,423,450 | 6/1995 | Shillington et al. . | |
| 5,482,095 | 1/1996 | De Chollet | 141/380 |
| 5,667,094 | 9/1997 | Rapchak et al. | 220/339 |

*Primary Examiner*—Paul T. Sewell
*Assistant Examiner*—Nhan T. Lam
*Attorney, Agent, or Firm*—Brian D. Bellamy

[57] ABSTRACT

A sharps disposal unit for use by paramedics and the like in the field that includes a container made of puncture resistant plastic or cloth and having an accordian like pleated side wall that stacks when compressed giving the container a very low profile before the container is stretched out for use. The container optionally slides into a holder that mounts to the side of a paramedic tool box for convient storage and location.

11 Claims, 6 Drawing Sheets

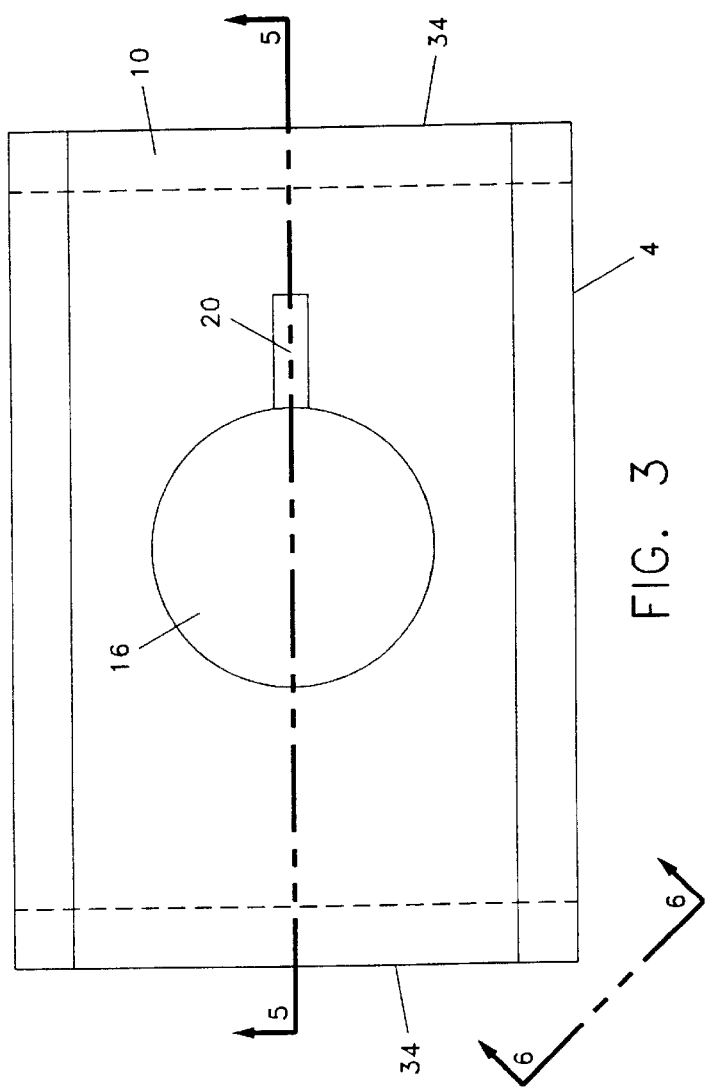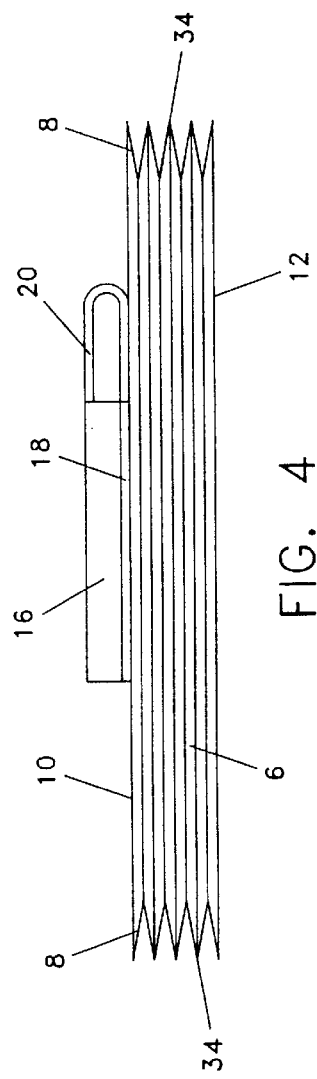

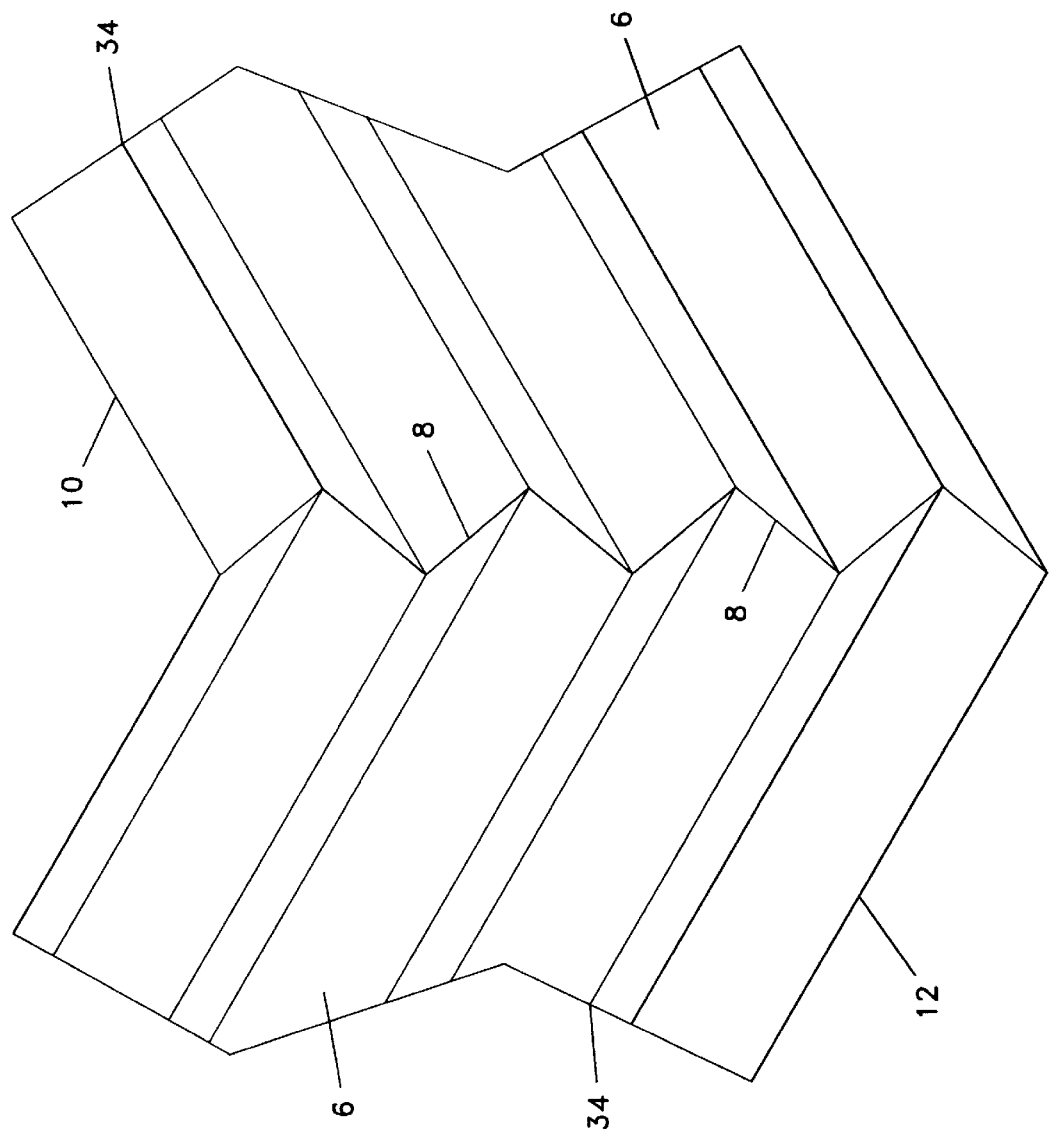

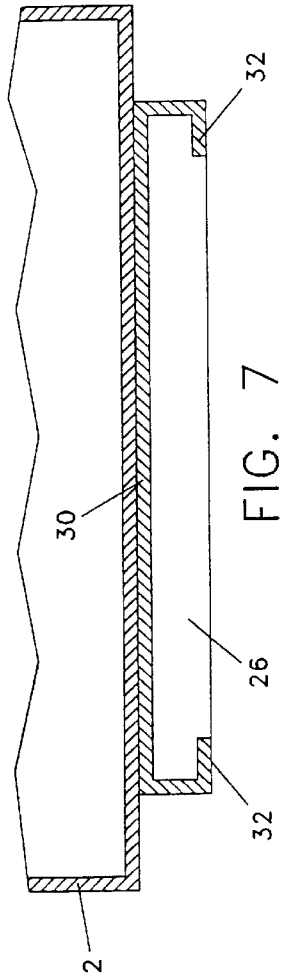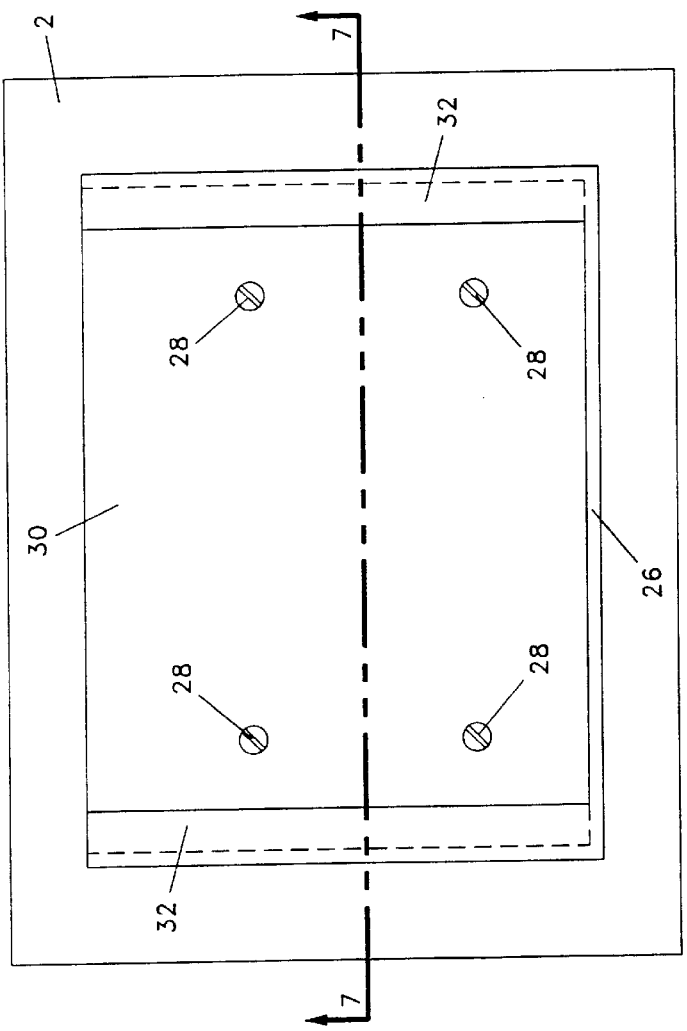

COLLAPSIBLE SHARPS CONTAINER WITH HOLDER

INTRODUCTION

The present application relates to a disposable container for medical sharps and biohazardous medical waste, and more particularly to a collapsible container and holder adapted for convenient accessibility and use by paramedics and the like in the field on emergency calls.

Medical sharps such as needles and syringes and biohazardous medical supplies such as used swabs and rags are often used in the field by paramedics and emergency medical technicians. While in the field paramedics work very rapidly and do not have time to make trips back and forth to an ambulance or supply station. Therefore, paramedics usually carry a single toolbox, also known as a jump box, that contains most of the supplies used by the paramedics in the field. The supplies include medical sharps and other materials that become hazardous once used on a patient. Often, these hazardous materials are not disposed of in presently available sharps containers because the paramedics do not find the containers convenient, and the paramedics do not want to make a separate trip to the ambulance to retrieve the sharps container. Furthermore, the current containers are rigid and bulky and are not designed for the level of transportability and convenience needed by paramedics in the field, and these known containers take up valuable space on an ambulance. Therefore, the hazardous materials created by paramedics in the field are often loosely disposed of by throwing them into the top of the paramedics toolbox for later clean-up. As a result, the hazardous materials will sometimes end up on the ground at the scene of the emergency or be dangerously tossed around in the paramedic's toolbox.

Accordingly, one object of the present invention is to provide a transportable puncture resistant sharps container that is economical and disposable, and yet which is conveniently accessible by paramedics in the field. Another object of the invention is to provide an attachment to a paramedic's toolbox that achieves the objects of the invention. A further object is to provide such a construction of the container of the invention that is collapsible and compact before the container is used. These and other objects and advantages of the present invention will become apparent to those persons skilled in the art from a study of the drawings and from a review of the following detailed description of a preferred embodiment of the invention.

BRIEF SUMMARY OF THE INVENTION

The present invention provides a sharps disposal unit for use by paramedics and the like in the field that includes a puncture resistant container having a side wall about the container's perimeter made of a puncture resistant plastic or cloth that is pleated and collapsible to a compacted size. The container has an opening in the top for receiving sharps and the like, and a lid connected to the top that is used for closing the container. The unit further includes a holder that is mounted onto a paramedic or EMT toolbox or the like that a bottom pleat of the pleated wall of the container slides into to temporarily attach the container to the toolbox with the container in it's collapsed state.

BRIEF DESCRIPTION OF THE DRAWINGS

The invention will be further described in connection with the accompanying drawings, in which:

FIG. 3 is a top view of the sharps container.

FIG. 4 is a side view of the sharps container in its collapsed state.

FIG. 6 is a partial section view of FIG. 3 taken along line 6—6 showing the construction of the pleated side wall of the container.

FIG. 7 is a horizontal section view of FIG. 8 taken along line 7—7 showing the construction of the holder.

FIG. 8 is a front view of the holder mounted on a toolbox.

DETAILED DESCRIPTION

Figure 1:
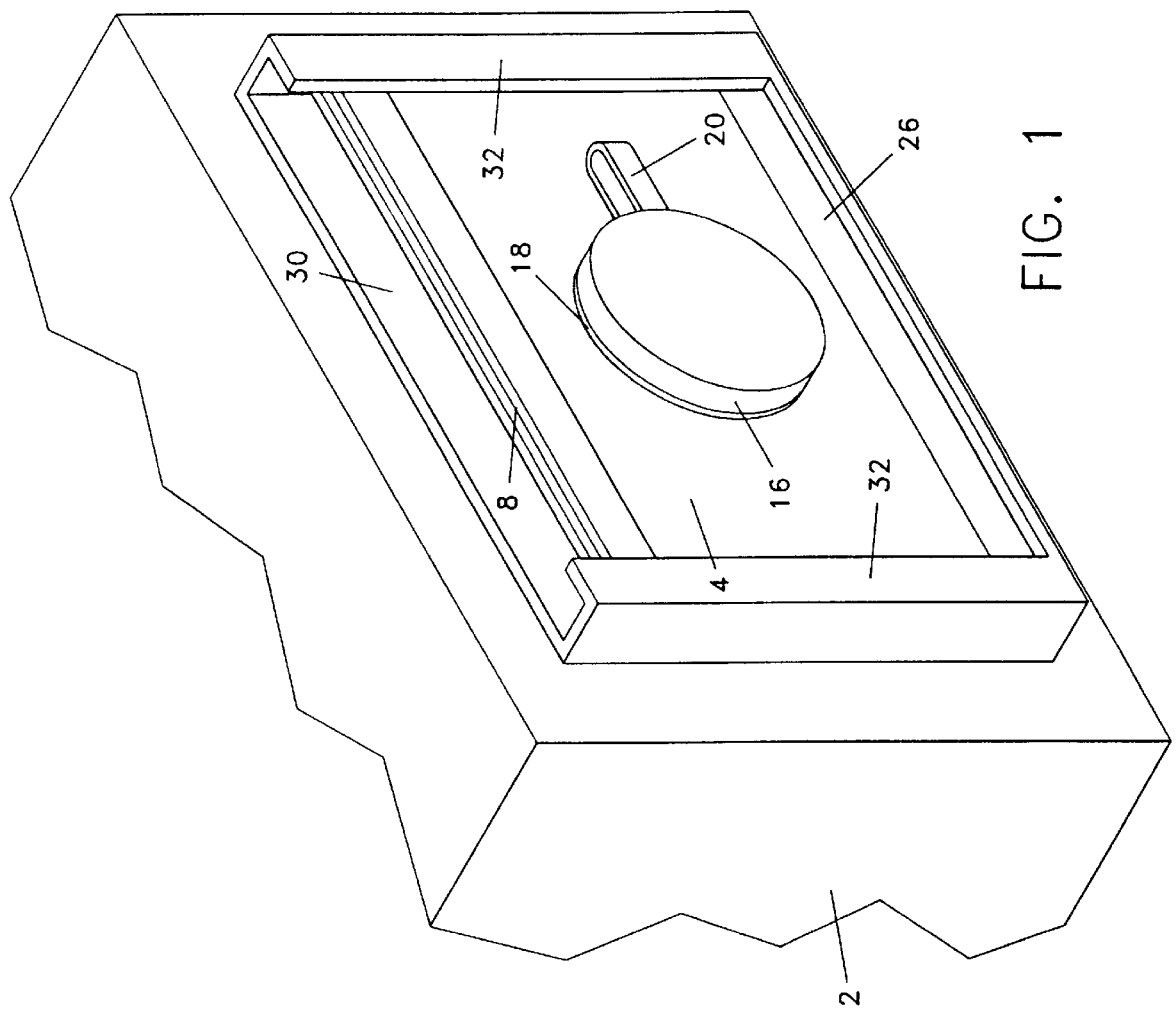
FIG. 1 is an elevational view of a collapsed sharps container and holder constructed in accordance with the teachings of the present invention and mounted to a toolbox.
Figure 2:
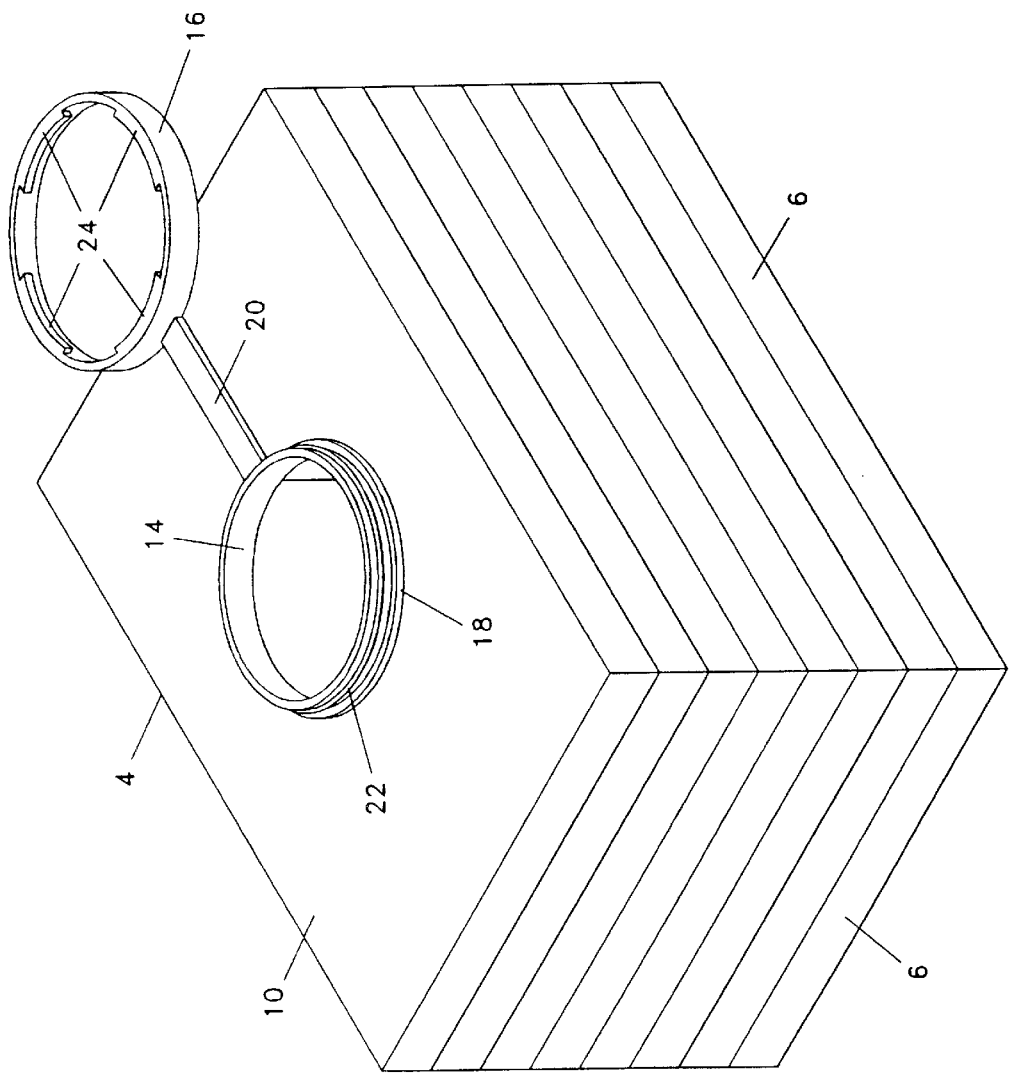
FIG. 2 is an elevational view of the sharps container in its extended state.

Referring to FIG. 1, an embodiment of the invention is shown. An Emergency Medical Technician and paramedic toolbox 2 is shown with a preferred embodiment of the invention mounted thereon at one end. A sharps container 4 is attached to the toolbox in a collapsed state. The container has an extensible side wall 6 about its entire side perimeter that is formed of a puncture resistant plastic or cloth. The wall is pleated with one or more creases therein to permit the wall to collapse into a flattened state as shown until the side wall of the container is extended for disposing of sharps. FIG. 2 shows the container in more detail with the side wall completely extended. In the particular example, the extensible side wall includes several pleats 8 or creases that permit the side wall to collapse when compressed. A wall having one pleat or more may satisfy the objectives of the present invention and the exact number of pleats used is not critical. The collapsible pleated side wall enables the container to be stored in a compact condition, which is very important for the convenient retention of the sharps unit on the paramedic toolbox prior to use. In the preferred embodiment, the container has a maximum height of about two inches or less when collapsed as shown in FIG. 4.

Figure 5:
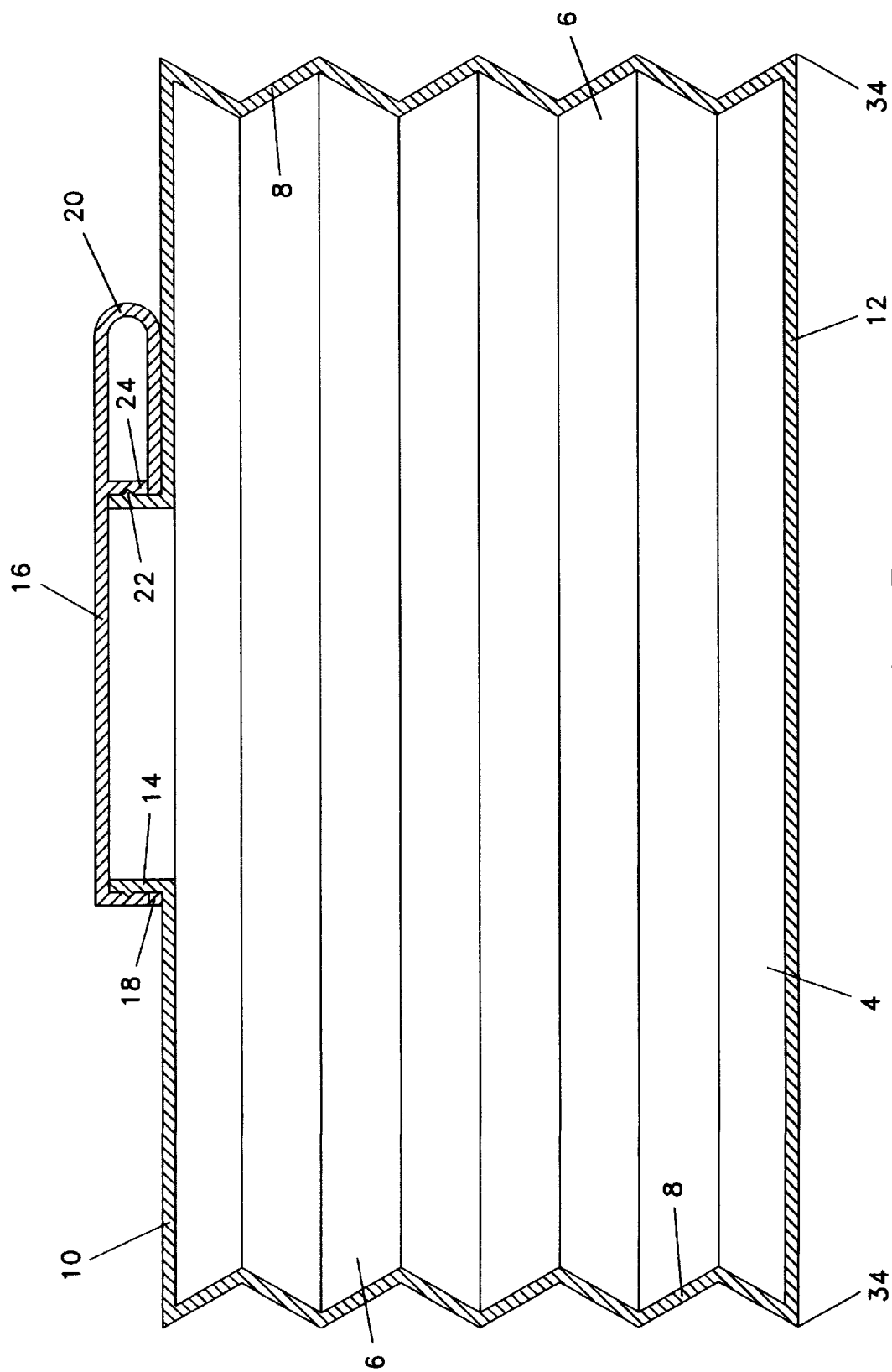
FIG. 5 is a section view of FIG. 3 taken along line 5—5, showing the construction of the neck and lid of the container.

The container includes a top wall 10 that has a short neck 14 extending therefrom, and the container has a bottom wall 12. Both the top wall and bottom wall are preferably made of a puncture resistant plastic and may be constructed of a thicker and more rigid material than the side wall 6. The neck of the top wall has a removable lid 16 attached thereto via a ring 18 that fits around the neck. A tab 20 connects the ring and lid. When the lid is closed and placed on the neck, the tab forms a small handle as shown in FIG. 5 that can be used to carry the container after it is filled. When detached from the neck, the lid hangs from the tab as shown in FIG. 2. When the lid is detached, medical sharps and other biohazardous waste can be discarded into the container. Referring to FIG. 3, the size of the preferred lid construction relative to the container is shown. With the lid removed, a large opening is formed in the top wall 10 of the container for receipt of medical waste. The large opening is advantageous for use in the field by paramedics where convenience is critical.

A cross-section of the container 4 and removable lid 16 attachment taken along line 5—5 of FIG. 3 is shown in FIG. 5 and shows the lid attachment in more detail. A preferred construction of the lid 16 is presented in which the ring 18 fits around the neck 14 of the container and is held onto the neck by a ridge 22 about the circumference of the neck. The lid includes several lips 24 about its inner rim. The lid fits about the neck and the lips facilitate holding the lid into place on the neck. Other lid constructions would be obvious to those skilled in the art and could be used without straying from the scope and teachings of the present invention to provide a removable lid construction for the container.

An important feature of the sharps disposal unit of the present invention is that the container 4 attaches to the toolbox via some suitable means such as the holder 26 that is affixed to one end of the toolbox 2. The combination of the holder and the compact size of the collapsed container make the container easily retained on a paramedic toolbox so that the container is conveniently available to paramedics while in the field on emergency calls. The means for affixing the holder to the toolbox could include screws 28 as shown in FIG. 8, an adhesive backing on the holder, or any desirable means.

FIGS. 7 and 8 further show that the holder of the preferred embodiment has a mounting surface 30 having at least one slot 32 on each side of the mounting surface that is formed by a flange extending from the edge of the mounting surface. The bottom edge of the mounting surface retains the container in a fixed position on the mounting surface. As shown, the slots 32 are formed by a flange that begins at the top corner of each side of the holder 26 and runs downward along the edges of the holder.

When the container 4 is collapsed, the pleats of the container fold to provide several protruding edges 34 on opposite sides of the container. The edges 34 may slide into the slots 32 such that the container is held within the holder until it is removed by sliding it out of the slots. Alternatively, the bottom protruding edges 34 on each side of the container may slide into the slot leaving the remainder of the container outside of the holder. Thereby, the holder could be made narrower. Likewise, the bottom protruding edges 34 may be provided by extending the bottom edge of the container beyond the perimeter of collapsed container such that those edges are especially adapted to be received by the holder 26. In each of the above permutations of the container, the container slides securely into the slots of the holder until the container stops at the bottom edge of the holder. Thereby, when the container is collapsed and attached to the holder on the side of an paramedic toolbox, it provides a compact and conveniently accessible sharps disposal container for paramedics.

I claim:

1. A sharps disposal unit for use by paramedics and the like comprising:
   (a) a container having:
      (i) a bottom wall;
      (ii) a pleated extensible side wall having a top end and a bottom end, the bottom end of the side wall attached to the bottom wall; and
      (iii) a top wall having an opening and the top wall attached to the top end of the side wall;
   (b) a means for covering the opening after medical sharps have been placed in the container; and
   (c) a means for temporarily holding the container while in a collapsed form on a medical tool box that includes:
      (i) a mounting surface;
      (ii) a means for affixing the mounting surface onto a medical tool box, and;
      (iii) a means for retaining the container on the mounting surface.

2. A sharps disposal unit as claimed in claim 1, in which the bottom wall and the top wall are made of a puncture resistant plastic material.

3. A sharps disposal unit as claimed in claim 1, in which the extensible side wall may be compressed such that the container has a maximum height of less than two inches.

4. A sharps disposal unit as claimed in claim 1, in which the top wall has a neck extending therefrom about the opening.

5. A sharps disposal unit as claimed in claim 4, in which the means for covering the opening further includes a removable lid connected to the neck.

6. A sharps disposal unit as claimed in claim 1, in which the extensible side wall is made of a puncture resistant plastic.

7. A sharps disposal unit as claimed in claim 1, in which the extensible side wall does not fully collapse under gravitational force when extended.

8. A sharps disposal unit for use by paramedics and the like comprising:
   (a) a container having:
      (i) a bottom wall;
      (ii) a pleated extensible side wall having a top end and a bottom end, the bottom end of the side wall attached to the bottom wall; and
      (iii) a top wall having an opening and the top wall attached to the top end of the side wall;
   (b) a means for covering the opening after medical sharps have been placed in the container; and
   (c) a means for temporarily holding the container while in a collapsed form on a medical tool box that includes: a mounting surface having a protruding bottom edge; at least one slot on each side of the mounting surface formed by a flange extending from the edge of the mounting surface; a means for mounting the holder onto a medical tool box.

9. A sharps disposal unit as claimed in claim 8, in which the container includes several protruding edges on opposite sides of the container such that when the collapsed container is placed onto the holder, the protruding edges slide into the slots.

10. A sharps disposal unit as claimed in claim 9, that further includes a means for retaining the container on the holder until the container is intentionally removed.

11. A sharps disposal unit for use by paramedics and the like comprising:
   (a) a container having:
      (i) a bottom wall made of a puncture resistant material;
      (ii) an pleated extensible side wall having a top end and a bottom end, the bottom end of the side wall attached to the bottom wall, and the side wall made of a puncture resistant material;
      (iii) a top wall attached to the top end of the side wall, and the top wall made of a puncture resistant material and having an opening therein for receiving medical sharps;
      (iv) several protruding edges about opposite sides of the container;
      (v) a neck that extends from the top wall about the opening;
   (b) a removable lid attached to the neck that covers the opening;
   (c) a holder having a mounting surface with at least one slot on each side of the mounting surface formed by flanges extending from opposite edges of the mounting surface such that the slots receive the protruding edges of the container; and
   (d) a means for mounting the holder onto a medical tool box.

* * * * *